(12) United States Patent
Gleeson et al.

(10) Patent No.: US 8,906,034 B2
(45) Date of Patent: Dec. 9, 2014

(54) INSTRUMENT AND METHOD FOR SPINAL COMPRESSION AND DISTRACTION

(71) Applicants: Garrett Gleeson, Encinitas, CA (US); Thomas Perry, Vista, CA (US); Nathan Meyer, Vista, CA (US); Anand Parikh, San Diego, CA (US); Clark Hutton, Carlsbad, CA (US)

(72) Inventors: Garrett Gleeson, Encinitas, CA (US); Thomas Perry, Vista, CA (US); Nathan Meyer, Vista, CA (US); Anand Parikh, San Diego, CA (US); Clark Hutton, Carlsbad, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 13/864,012

(22) Filed: Apr. 16, 2013

(65) Prior Publication Data

US 2013/0289633 A1    Oct. 31, 2013

Related U.S. Application Data

(60) Provisional application No. 61/625,264, filed on Apr. 17, 2012.

(51) Int. Cl.
*A61B 17/58* (2006.01)
*A61B 17/70* (2006.01)

(52) U.S. Cl.
CPC .......... *A61B 17/7074* (2013.01); *A61B 17/708* (2013.01)

USPC .......................................... 606/99; 606/86 A

(58) Field of Classification Search
USPC ............... 606/279, 86 R, 86 A, 105
See application file for complete search history.

(56) References Cited

U.S. PATENT DOCUMENTS

| | | | |
|---|---|---|---|
| 4,733,657 A | 3/1988 | Kluger | |
| 4,957,495 A | 9/1990 | Kluger | |
| 7,008,432 B2 | 3/2006 | Schlapfer et al. | |
| 7,776,051 B2 | 8/2010 | Colleran et al. | |
| 8,394,109 B2 | 3/2013 | Hutton et al. | |
| 2005/0131421 A1 | 6/2005 | Anderson et al. | |
| 2005/0245928 A1 | 11/2005 | Colleran et al. | |
| 2006/0036244 A1 | 2/2006 | Spitler et al. | |
| 2006/0247645 A1* | 11/2006 | Wilcox et al. | 606/86 |
| 2008/0077155 A1* | 3/2008 | Diederich et al. | 606/105 |
| 2010/0036443 A1 | 2/2010 | Hutton et al. | |
| 2011/0130793 A1 | 6/2011 | Woolley et al. | |

* cited by examiner

*Primary Examiner* — Mary Hoffman
*Assistant Examiner* — Tara Carter
(74) *Attorney, Agent, or Firm* — Michael J. Loi

(57) ABSTRACT

An orthopedic instrument for compression and distraction of bone segments includes a first receiver, a second receiver, a positioner member, and a guide member. The first receiver includes a first receiver aperture that receives a first screw extender. The second receiver includes a second extender aperture that receives a second screw extender. The positioner member translates the second receiver relative to the first receiver to apply one of a compression and a distraction force on the screw extenders. The guide member parallel to the positioner member guides the second receiver relative to the first receiver.

8 Claims, 14 Drawing Sheets

INSTRUMENT AND METHOD FOR SPINAL COMPRESSION AND DISTRACTION

FIELD

The present invention relates to surgical methods and devices for spinal surgery, and in particular to instruments and methods for applying compression and/or distraction forces to the spine.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae.

The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. If the proper shaping and/or curvature are not present due to scoliosis, neuromuscular disease, cerebral palsy, or other disorder, it may be necessary to straighten or adjust the spine into a proper curvature.

Generally the correct curvature is obtained by manipulating the vertebrae into their proper position and securing that position with a rigid system of screws and rods. The screws may be inserted into the pedicles of the vertebrae to act as bone anchors, and the rods may be inserted into heads of the screws. Two rods may run substantially parallel to the spine and secure the spine in the desired shape and curvature. Thus the rods, which are shaped to mimic the correct spinal curvature, force the spine into proper alignment. Bone grafts are then placed between the vertebrae and aid in fusion of the individual vertebrae together to form a correctly aligned spine.

In many surgical spinal procedures, such as, for example, the correction of scoliosis, nerve root decompression, interbody fusion, repair of kyphosis and treatment of other spinal defects or trauma, it is desirable or necessary to supply forces by compression and/or distraction in the defective region. While there are devices that exist for applying forces to the spine, there remains a need for devices and methods that improve surgeon efficiency and provide the surgeon additional options in the application of such forces. The present invention is directed toward meeting these needs, among others.

SUMMARY

An orthopedic instrument for compression and distraction of bone segments includes a first receiver, a second receiver, a positioner member, and a guide member. The first receiver includes a first receiver aperture that receives a first screw extender. The second receiver includes a second extender aperture that receives a second screw extender. The positioner member translates the second receiver relative to the first receiver to apply one of a compression and a distraction force on the screw extenders. The guide member parallel to the positioner member guides the second receiver relative to the first receiver.

In other features, at least one of the first and second receivers includes a rotatable portion that receives one of the first and second screw extenders and rotates relative to a fixed portion in a rotatable configuration and locks relative to the fixed portion in a locked configuration. A lock member locks the rotatable portion with the fixed portion in the locked configuration and unlocks the rotatable portion from the fixed portion in the rotatable configuration. At least one of the first and second receivers includes a released configuration for freely sliding along the positioner member and an engaged configuration for threaded engagement with the positioner member. A release member disengages an internal thread of the at least one receiver from an external thread of the positioner member in the released configuration and engages the internal thread with the external thread in the engaged configuration.

An instrument for compression and distraction of vertebrae using screw extenders includes a first receiver, a second receiver, a positioner member, and a guide member. The first receiver includes a fixed portion with a first positioner aperture and a first guide aperture and a rotatable portion with a first receiver aperture for attachment to a first screw extender. The second receiver includes a second positioner aperture, a second guide aperture, and a second receiver aperture for attachment to a second extender. The positioner member translates one of the first and second receivers relative to the other of the first and second receivers. The guide member guides the translation of the one of the first and second receivers relative to the other of the first and second receivers.

In other features, the positioner member includes a shaft with a threaded portion and the guide member is substantially parallel to the positioner member. The rotatable portion is rotatable relative to the fixed portion in a rotatable configuration and is rotatably fixed relative to the fixed portion in a fixed configuration. A lock member disengages the rotatable portion from the fixed portion in the rotatable configuration and engages the rotatable portion with the fixed portion in the fixed configuration. The lock member includes a lock shaft extending through a first lock aperture of the fixed portion and pivotally couples with a lever arm at a first end and a lock cap at a second end within a second lock aperture of the rotatable portion. The fixed portion includes a first surface with a first plurality of projections that mates with a second plurality of projections on a second surface of the rotatable portion.

In still other features, the second receiver freely slides along the positioner member and guide member when the release member is in a released configuration and threadably moves along the positioner member in an engaged configuration. A release member disengages the second receiver from the positioner member in the released configuration and engages the second receiver with the positioner member in the engaged configuration. The release member includes a partially threaded sleeve slidably extending through a release aperture of the second receiver and coupled with a release button and bias spring that biases the release member into the engaged configuration.

An instrument for compression and distraction of vertebrae using screw extenders includes a translatable receiver, a non-translatable receiver, a guide member, a positioner member, first and second lock members, and a release member. The translatable receiver includes a translatable portion and a first rotatable portion with a first extender aperture configured to receive a first screw extender. The non-translatable receiver includes a non-translatable portion and a second rotatable portion with a second extender aperture configured to receive a second screw extender.

The guide member includes a first end coupled with the non-translatable portion and a second end slidably coupled with the translatable portion. The positioner member includes a first end rotatably coupled with the non-translatable portion and a second end threadedly coupled with the translatable portion. The first and second lock members lock the first and second rotatable portions at first and second predetermined angles relative to the guide member in a locked configuration and permit rotation of the first and second rotatable portions relative to the guide member in an unlocked configuration.

The release member couples the translatable receiver with the positioner member. The release member includes a sleeve and a bias member. The sleeve includes a threaded portion and a non-threaded portion that slides within the translatable portion. The bias member biases the threaded portion of the sleeve into threaded engagement with the positioner member in an engaged configuration and disengages the threaded portion from the positioner member when moved to a slidable configuration.

DETAILED DESCRIPTION

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Figure 1:
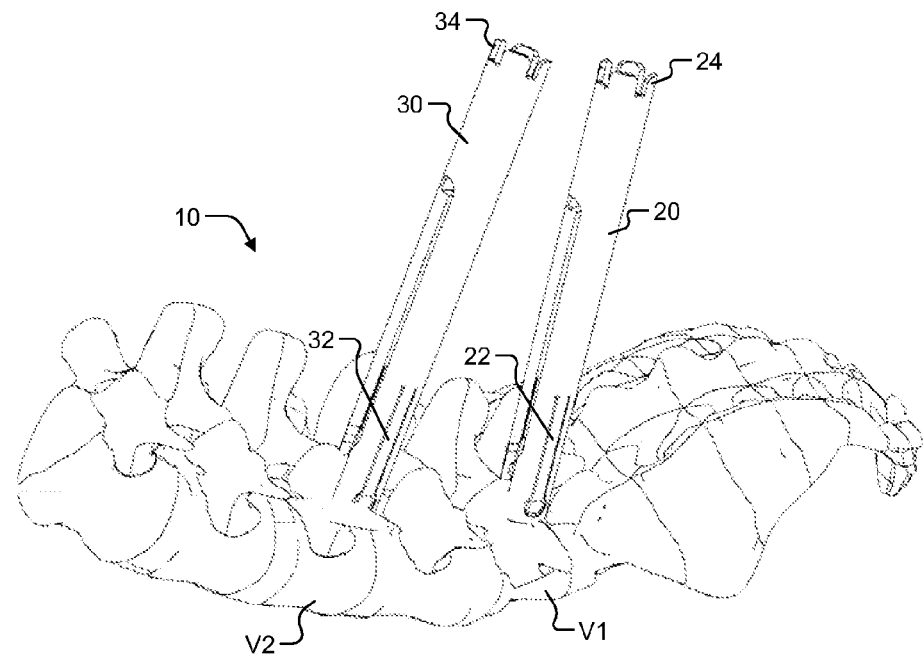
FIG. 1 is a perspective view of a portion of a spinal column including attached screw extenders.

FIG. 1 illustrates a perspective view of a portion of a spinal column 10 including a first vertebra V1 and a second vertebra V2. Although the portion shown includes the lumbar and sacral regions of the spinal column 10, the invention of the present disclosure may be used in other regions including the cervical and thoracic regions of the spine. Screws may be inserted into the first and second vertebrae V1 and V2 through minimally invasive surgery. For example, the screws may be inserted into the pedicles of the vertebrae. Subsequently, additional instrumentation may be inserted to manipulate the vertebrae into proper alignment, to reduce deformity, and to compress or distract the vertebrae.

Continuing with FIG. 1, a first screw extender 20 may be attached to a first screw (not shown) inserted into the first vertebra V1. A second screw extender 30 may be attached to a second screw (not shown) inserted into the second vertebra V2. At distal ends, the extenders 20, 30 may include various features, such as elastically flexible tabs 22, 32, configured to attach to portions of the screws. The screw extenders 20, 30 may include any type of attachment feature necessary to attach to the screws. At their proximal ends, the extenders 20, 30 may include various features, such as tabs 24, 34, configured to attach to instruments.

For ease of discussion, the screw extenders 20, 30 may be used to rotate and position the first vertebra V1 relative to the second vertebra V2. The screw extenders 20, 30 may extend outside the surgical site to enable attachment of various devices, including the instrument of the present disclosure. The screw extenders 20, 30 may include cannulae for insertion of setscrews and screw drivers. Other extension members or elongated portions of the screws are also contemplated. For example, derotation or reduction instruments including various extension tubes or elongated members may also couple to the screws and extend proximally from the surgical site. Exemplary systems of screws and screw extenders may be found in U.S. Pub. No. 2009/0171391 and U.S. Pub. No. 2010/0036443.

Figure 2:
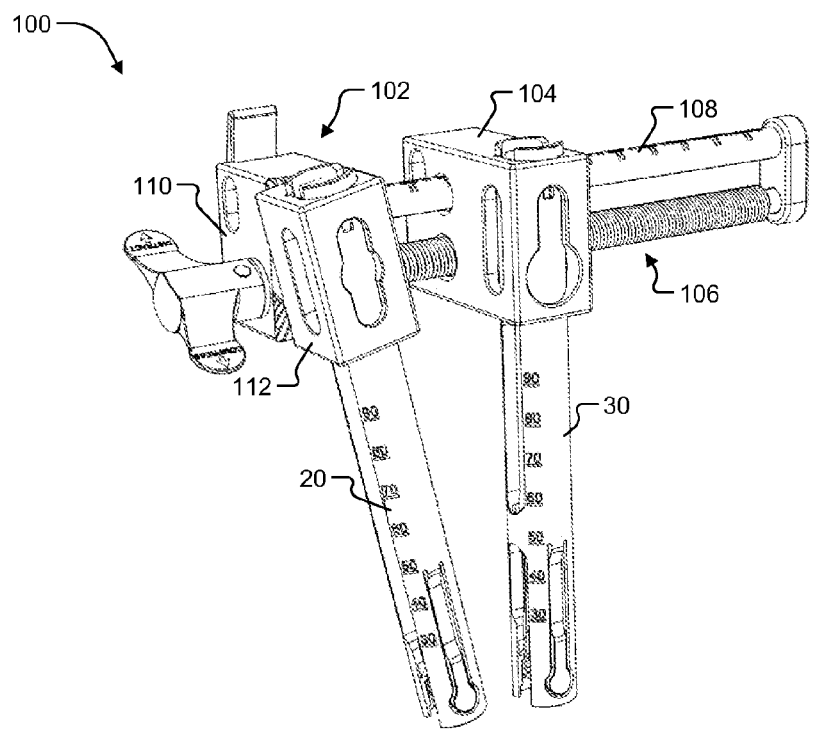
FIG. 2 is a perspective view of an exemplary instrument for compression and distraction of the spinal column using the screw extenders of FIG. 1 according to the principles of the present disclosure.
Figure 3:
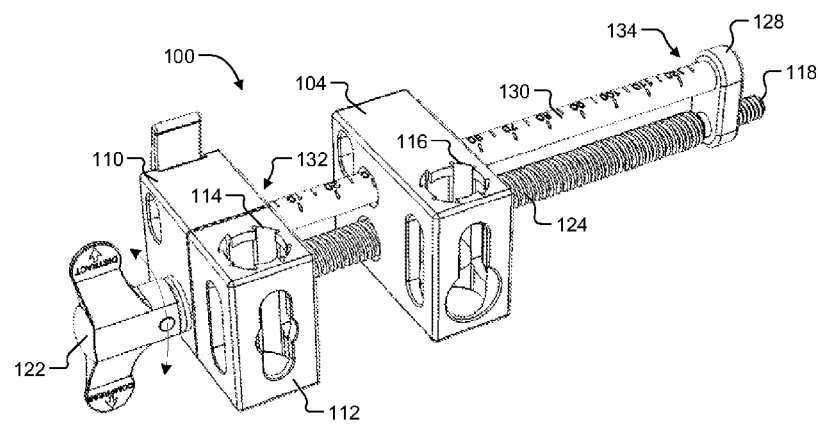
FIG. 3 is a perspective view of the instrument according to the principles of the present disclosure.
Figure 4:
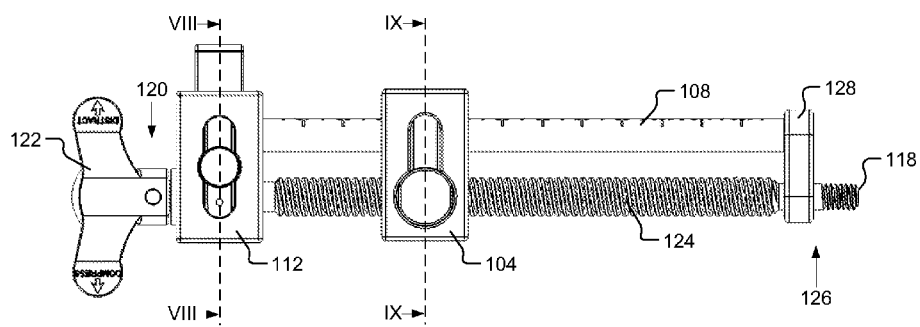
FIG. 4 is a front view of the instrument according to the principles of the present disclosure.

FIG. 2 illustrates a perspective view of an exemplary instrument 100 for compression and distraction of the vertebrae V1 and V2 of the spinal column 10 according to the principles of the present disclosure. The instrument 100 includes a first receiver 102, a second receiver 104, and a positioner member 106. The first receiver 102 may attach to the first extender 20 and the second receiver 104 may attach to the second extender 30 of FIG. 1. The extenders 20, 30 may include various features that limit rotational or translational movement when attached to the instrument 100. For example, as shown in FIG. 1, the tabs 24, 34 may engage with features of the receivers 102 and 104 described herein. The positioner member 106 may position at least one of the first and second receivers 102 and 104. For example, the positioner member 106 may translate the second receiver 104 relative to the first receiver 102. A guide member 108 may guide the movement of at least one of the first and second receivers 102 and 104. For example, the guide member 108 may extend parallel to the positioner member 106 and through the second receiver 104 to guide its movement relative to the first receiver 102. The first receiver 102 may further include a fixed portion 110 and a rotatable portion 112. The rotatable portion 112 may rotate or pivot to various angles relative to the fixed portion 110.

FIGS. 3-7 illustrate additional features of the instrument 100 that provide greater flexibility for attachment of the extenders 20 and 30 as well as positioning and angulation to provide appropriate compression and distraction forces on the vertebrae V1 and V2. The rotatable portion 112 may include a first extension member aperture 114 for receiving the first extender 20. The second receiver 104 may include a second extension member aperture 116 for receiving the second extender 30. The fixed portion 110 and second receiver 104 may receive the positioner member 106 and the guide member 108. The positioner member 106 positions the second receiver 104 relative to the first receiver 102 in a first direction along a longitudinal axis of the positioner member 106. The guide member 108 guides the second receiver 104 and prevents rotation about the positioner member 106 as it rotates to position the second receiver 104.

The positioner member 106 may include a first shaft 118 with a first end 120 that extends through the first receiver 102 and terminates in an adjuster 122 or knob. The first end 120 may rotate freely within the first receiver 102. The adjuster 122 may be used to rotate the positioner member 106. The adjuster 122 may be secured to the first end 120 with a lock pin. The shaft 118 may include a threaded portion 124 that engages with features within the second receiver 104. The threaded portion 124 may rotate in a first direction to position the second receiver 104 away from the first receiver 102 and a second opposite direction to position the second receiver 104 towards the first receiver 102. A second end 126 of the positioner member 106 may couple with an end coupler 128. The second end 126 may rotate freely within the end coupler 128.

The guide member 108 extends through the first and second receivers 102 and 104 and guides the movement of the second receiver 104. The guide member 108 may include a second shaft 130 with a first end 132 received by the first receiver 102. The second shaft 130 may include a substantially smooth, cylindrical surface. The first end 132 may be secured within the first receiver 102 with a lock pin. The guide member 108 extends away from the first receiver 102 and through the second receiver 104 substantially parallel to the positioner member 106. A second end 134 of the second shaft 130 may couple with the end coupler 128. The second end 134 may be secured by the end coupler 128. The shaft 130 may include markings indicating distances between the first and second receivers 102 and 104.

Figure 5:
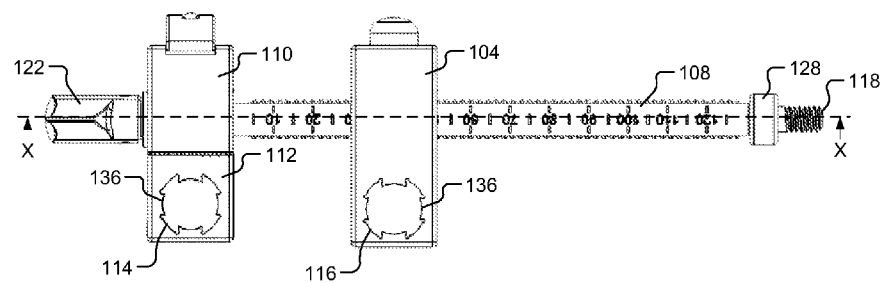
FIG. 5 is a top view of the instrument according to the principles of the present disclosure.

The instrument 100 may include attachment features for quick attachment to and removal from the extenders 20 and 30. For example, as illustrated in FIG. 5, radial tabs 136 may extend radially inward from sidewalls of the apertures 114 and 116. The radial tabs 136 may be configured to engage the proximally extending tabs 24 and 34 on the proximal ends of the first and second extenders 20 and 30. Each aperture may include a plurality of radial tabs 136. For example, the radial tabs 136 may be aligned at approximately 90 degree intervals around the apertures 114 and 116. The tabs 136 may restrict rotation of the extenders 20 and 30 within the apertures 114 and 116.

Figure 6:
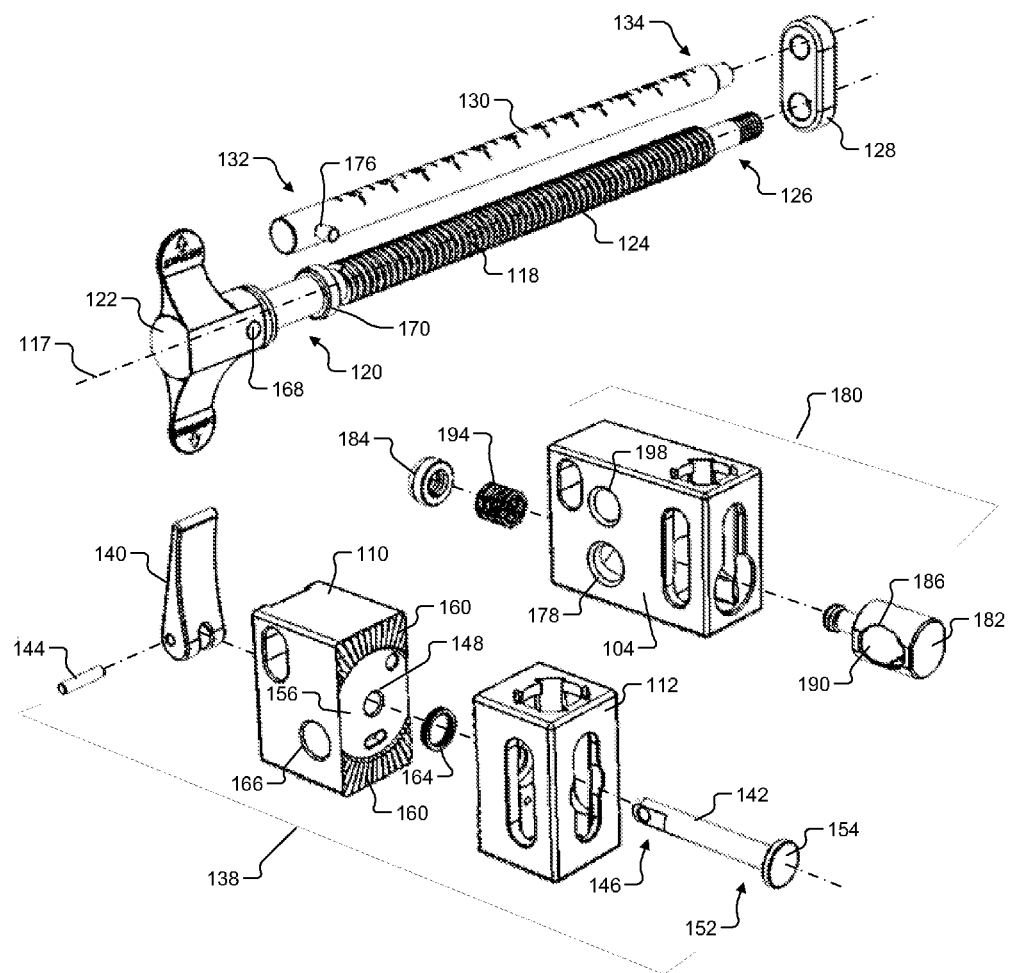
FIG. 6 is an exploded perspective view of the instrument according to the principles of the present disclosure.
Figure 7:
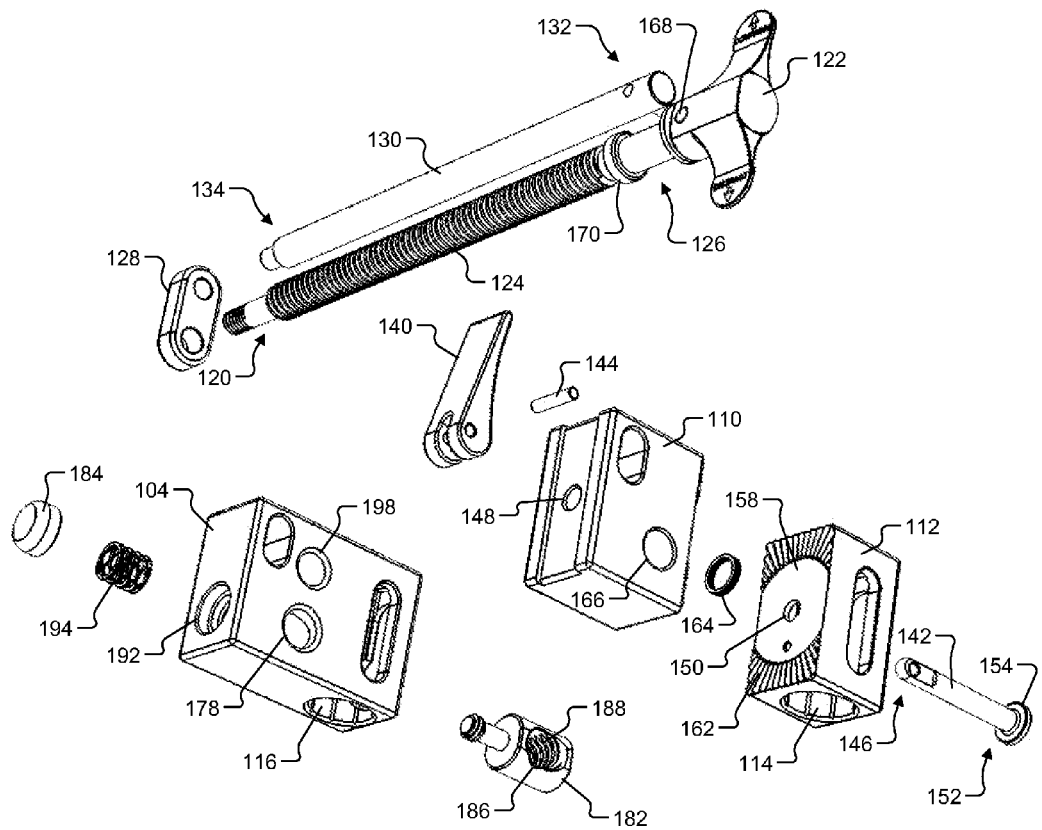
FIG. 7 is an exploded perspective view of the instrument according to the principles of the present disclosure.

FIGS. 6 and 7 are exploded views of the instrument 100 illustrating various examples of features that permit the rotational positioning of the first receiver 102. For example, the first receiver 102 includes the rotatable portion 112 and the fixed portion 110. A lock member 138 may couple the fixed portion 110 and the rotatable portion 112. The lock member 138 may include a lock arm 140 and a lock shaft 142. The lock shaft 142 may extend through the fixed portion 110 and the rotatable portion 112 of the first receiver 102. A lock pin 144 may pivotally couple the lock arm 140 with the lock shaft 142. The lock arm 140 may engage the fixed portion 110 as it pivots about the lock pin 144. The lock pin 144 may be located off-center at a base portion of the lock arm 140. For example, as the lock arm 140 rotates, the lock pin 144 may translate towards or away from the fixed portion 110, thus moving the attached lock shaft 142 within the fixed portion 110.

Figure 8:
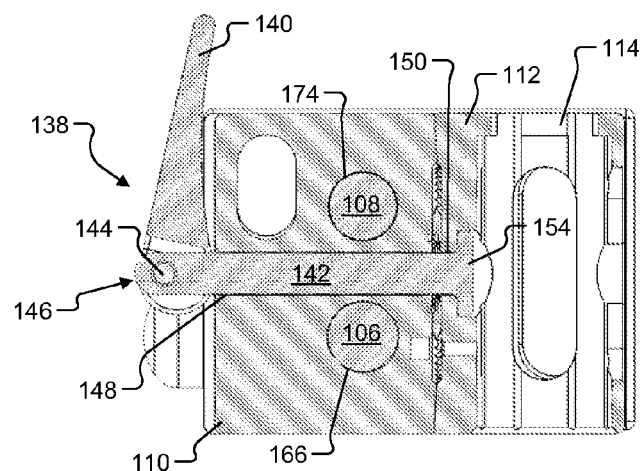
FIG. 8 is a cross-sectional view of the instrument of FIG. 4 looking into a plane VIII according to the principles of the present disclosure.

Referring also to FIG. 8, a first end 146 of the lock shaft 142 may extend through a first lock aperture 148 in the fixed portion 110 and a second lock aperture 150 in the rotatable portion 112. The first end 146 of the lock shaft 142 may include a diameter less than or equal to a diameter of the first and second lock apertures 148 and 150 to permit sliding engagement therein. A second end 152 of the lock shaft 142 may extend outside the second lock aperture 150 and terminate in a lock cap 154. The lock cap 154 may include a diameter greater than the diameter of the first and second lock apertures 144 and 146 to prevent the second end 142 of the lock shaft 142 from passing therethrough. The rotatable portion 112 may rotate about the lock shaft 142.

The lock arm 140 may be used to actuate the lock member 138 and position the rotatable portion 112 relative to the fixed portion 110. For example, the lock member 138 may position the rotatable portion 112 between a locked configuration shown in FIGS. 11 and 12 and a rotatable configuration with the fixed portion 110 shown in FIGS. 13 and 14. The fixed portion 110 may include a first surface 156 that mates with a second surface 158 of the rotatable portion 112. In FIG. 6, the first surface 156 includes a first set of projections 160 extending towards the rotatable portion 112. In FIG. 7, the second surface 158 includes a second set of projections 162 extending towards the fixed portion 110. The first and second sets of projections 160 and 162 may extend radially from the first and second lock apertures 148 and 150 respectively. A bias device 164, such as a spring may bias the rotatable portion 112 away from the fixed portion 110.

Figure 11:
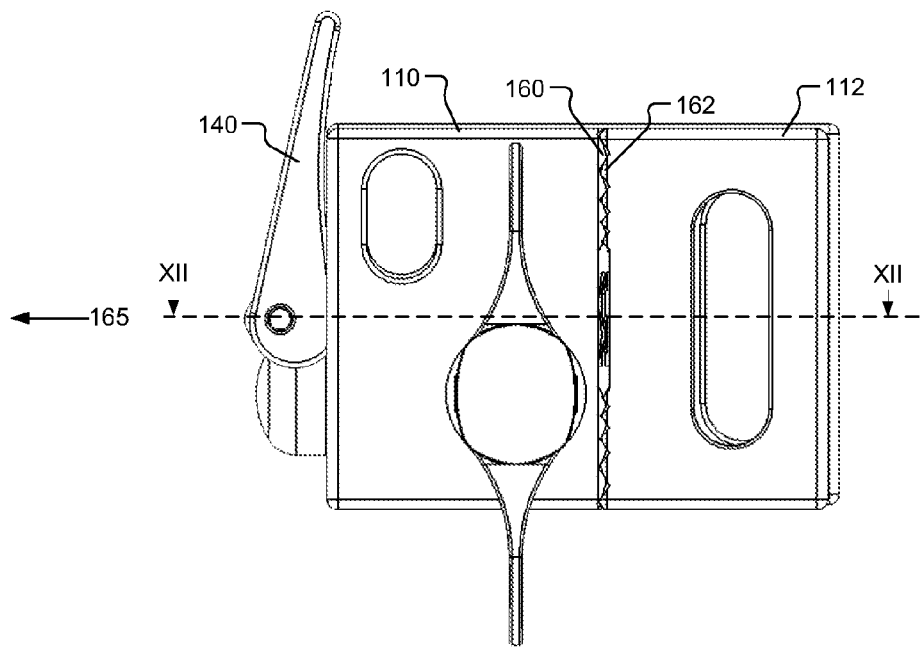
FIG. 11 is a side view of the instrument according to the principles of the present disclosure.
Figure 12:
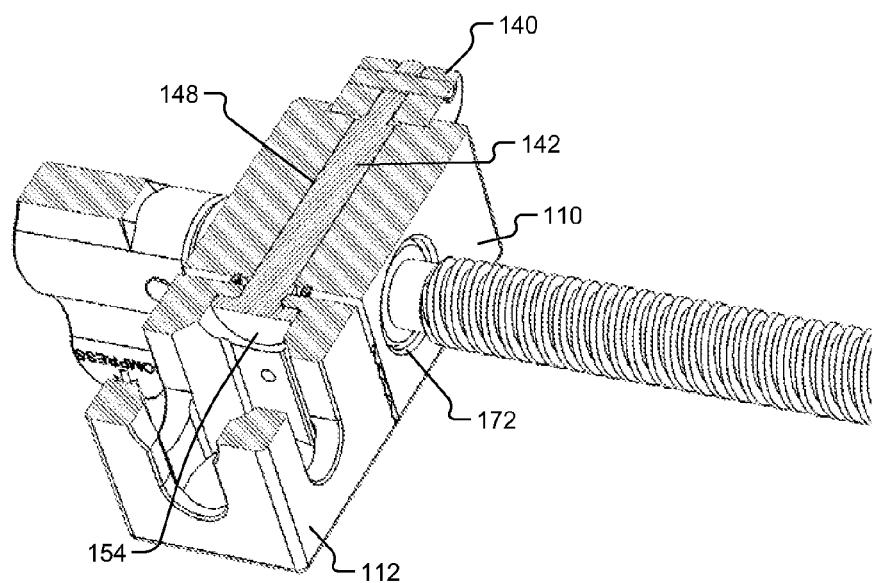
FIG. 12 is a partial cross-sectional view of the instrument of FIG. 11 looking into a plane XII according to the principles of the present disclosure.
Figure 13:
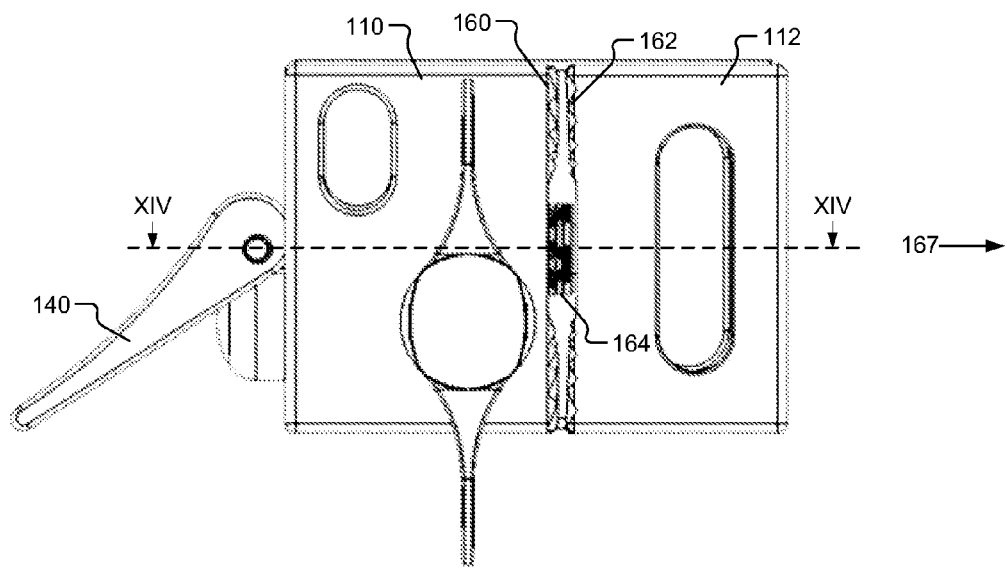
FIG. 13 is a side view of the instrument according to the principles of the present disclosure.
Figure 14:
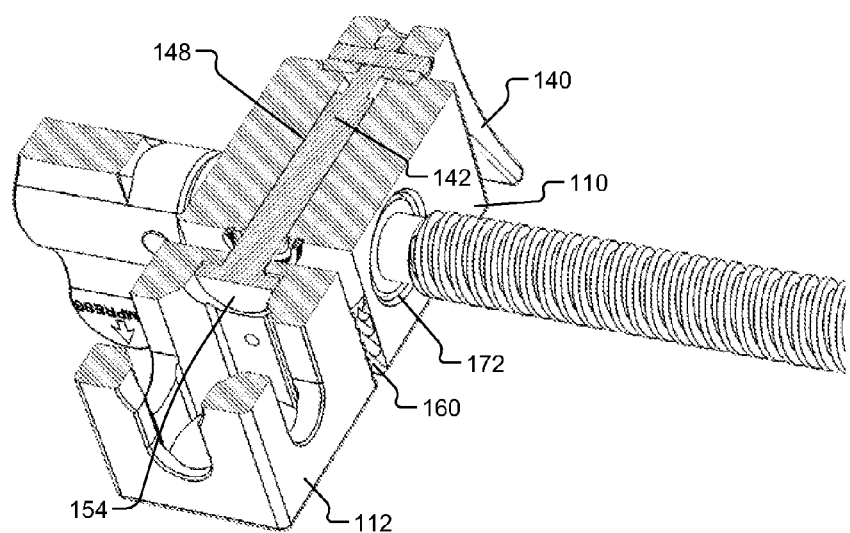
FIG. 14 is a partial cross-sectional view of the instrument of FIG. 13 looking into a plane XIV according to the principles of the present disclosure.

In FIGS. 11 and 12, the lock member 138 positions the fixed portion 110 and the rotatable portion 112 in the locked configuration. The lock arm 140 applies force to pull on the lock shaft 142 in a first direction 165. The lock shaft 142 pulls on the lock cap 154 within the second lock aperture 150. The lock cap 154, having a larger diameter than the second lock aperture 150, may not pass through the second lock aperture 150. The lock cap 154 thus transfers the force to the rotatable portion 112 to pull the rotatable portion 112 towards the fixed portion 110. Thus, the fixed portion 110 engages the rotatable portion 112. The first set of projections 160 engages the second set of projections 162 to prevent rotation of the rotatable portion 112 relative to the fixed portion 110. In FIGS. 13 and 14, the lock member 138 positions the fixed portion 110 and the rotatable portion 112 in the rotatable configuration. The lock arm 140 rotates and reduces force on the lock shaft 142. The bias spring 164 may bias the rotatable portion 112 away from the fixed portion 110 in a second direction 167. The first set of projections 160 disengages the second set of projections 162 to allow rotation of the rotatable portion 112 relative to the fixed portion 110.

Figure 15:
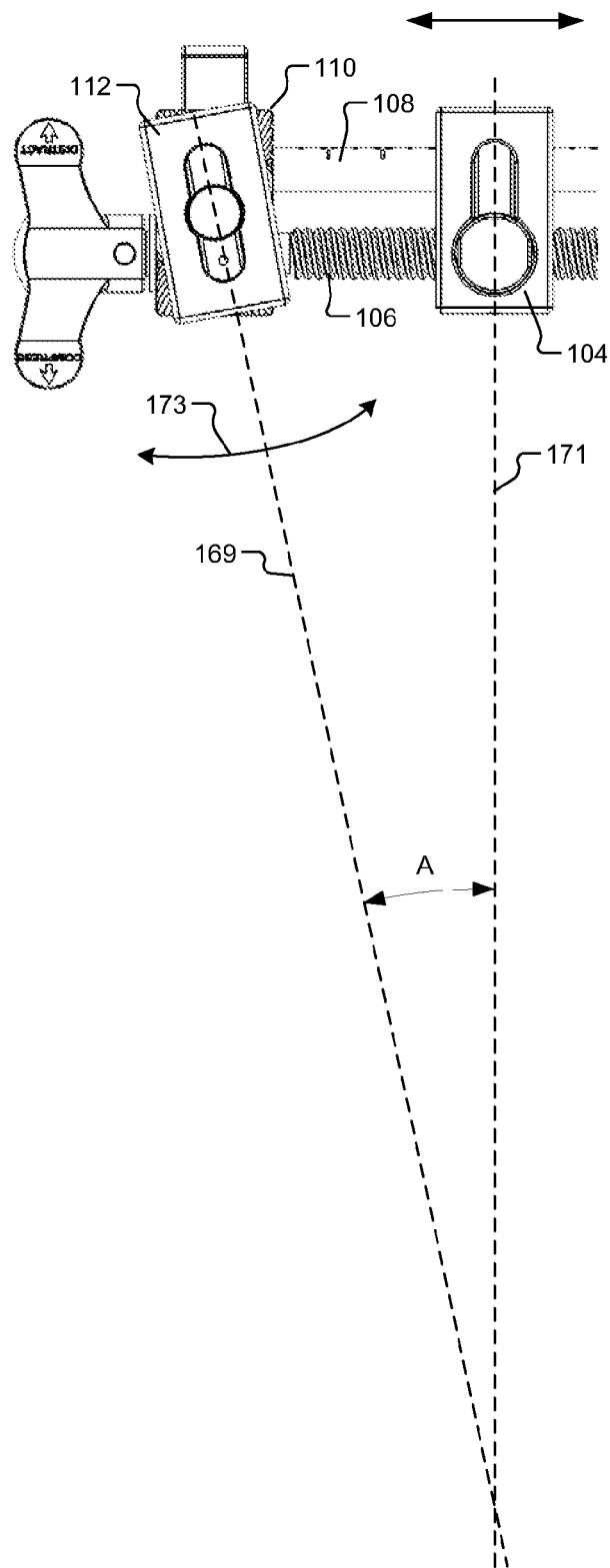
FIG. 15 is a partial front view of the instrument according to the principles of the present disclosure.

Referring now to FIG. 15, the first receiver 102 may be positioned at various angles relative to the second receiver 104. For example, the lock member 138 may position the rotatable portion 112 and fixed portion 110 in the rotatable configuration. A surgeon may then rotate the rotatable portion 112 about the lock shaft 142. In FIG. 15, a longitudinal axis 169 of the first extension aperture 114 may include an angle A relative to a longitudinal axis 171 of the second extension aperture 116. The angle A may be adjusted by rotating the rotatable portion 112 as shown by arrow 173 and translating the second receiver 104 as shown by arrow 175.

Continuing with FIGS. 6 and 7, the exploded views of the instrument 100 illustrate various examples of features that facilitate the translational positioning of the second receiver 104 relative to the first receiver 102. For example, the first receiver 102 and second receiver 104 include various apertures and/or bores to receive the positioner member 106 and guide member 108.

Figure 10:
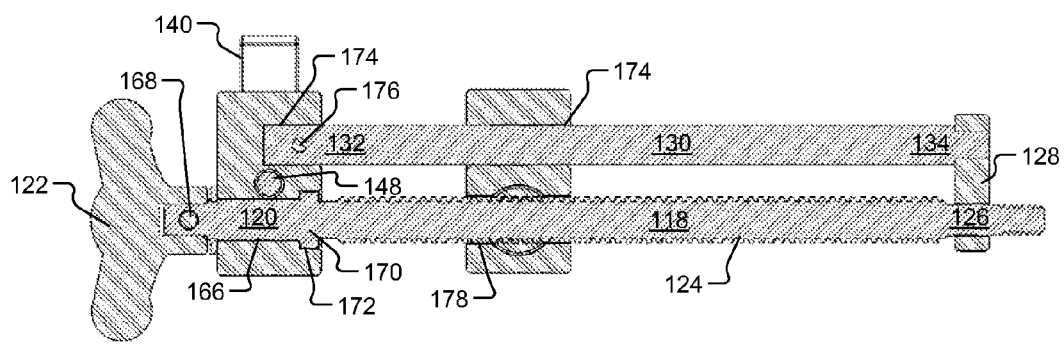
FIG. 10 is a cross-sectional view of the instrument of FIG. 5 looking into a plane X according to the principles of the present disclosure.

Referring now also to the cross-sectional views of FIGS. 8 and 10, a first positioner aperture 166 extends through the fixed portion 110 of the first receiver 102. The first positioner aperture 166 may extend transverse to the first lock aperture 148. The first positioner aperture 166 may be disposed distal to the first lock aperture 148. The first positioner aperture 166 may receive the first end 120 of the positioner member 106. The first end 120 may include a smooth, cylindrical outer surface that rotates freely within the first positioner aperture 166. The first end 120 may extend outside the first positioner aperture 166 to couple with the adjuster 122 via a removable pin 168. A retaining member 170 on the shaft 118 may retain the first end 120 of the positioner member 106 within the opposite end of the first lock aperture 148 as illustrated in FIGS. 12 and 14. For example, a clip or guide wheel may rotate within a widened portion 172 of the first positioner aperture 166.

A first guide aperture 174 extends into the fixed portion of the first receiver 102. The first guide aperture 174 may extend transverse to the first lock aperture 148 and parallel to the first positioner aperture 166. The first guide aperture 174 may be disposed proximal to the first lock aperture 148. The first guide aperture 174 may receive the first end 132 of the guide member 108. The first end 132 may include a smooth, cylindrical outer surface that rotates freely within the first guide aperture 174. In other examples, an anti-rotation pin 176 may lock the guide member 108 to prevent rotation. The first end 132 may be locked within the fixed portion 110 of the first receiver by the pin 176.

Figure 9:
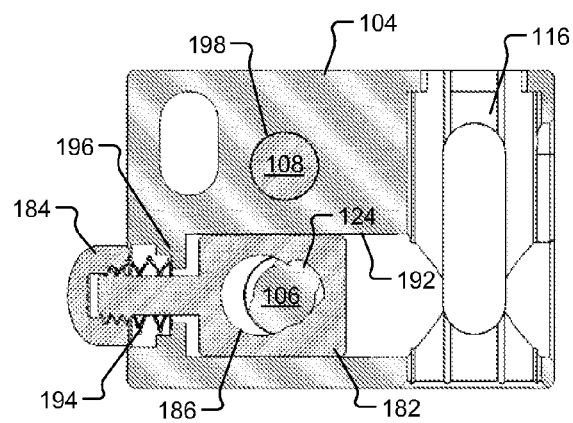
FIG. 9 is a cross-sectional view of the instrument of FIG. 4 looking into a plane IX according to the principles of the present disclosure.

Similarly, a second positioner aperture 178 extends through the second receiver 104. The second positioner aperture 178 may receive the threaded portion 124 of the positioner member 106. The second end 126 of the positioner member 106 may extend outside the second positioner aperture 178. The second end 126 may include a smooth, cylindrical outer surface that rotates freely within the end coupler 128. The second receiver 104 further includes a release member 180 for releasably engaging the positioner member 106, shown in detail in the cross-sectional view of FIG. 9.

The release member 180 may include a sleeve 182 and a release actuator 184. The sleeve 182 may include a thru-hole 186 that receives the threaded portion 124 of the positioner member 106. The thru-hole 186 may be formed from two separate, intersecting bores. A first bore may be tapped and a second bore may be smooth. For example, the thru-hole 186 may include a threaded portion 188 and a non-threaded portion 190. The threaded portion 188 and the non-threaded portion 190 may be disposed on opposite sides of the thru-hole 182. The release member 180 may slide within a release aperture 192 inside the second receiver 104. The release aperture 192 may communicate with the second positioner aperture 178. The release aperture 192 may extend transverse to the second positioner aperture. A release spring 194 within the release aperture 192 may bias the release member 180. The release spring 194 may engage the release actuator 184 and a narrowed portion 196 or internal ridge of the release aperture 192. The thru-hole 186 may align with the second positioner aperture 178 to permit passage of the positioner member 106 there through.

A second guide aperture 198 through the second receiver 104. The second guide aperture 198 may extend transverse to the release aperture 192 and parallel to the second positioner aperture 178. The second guide aperture 198 may be disposed proximal to the release aperture 192. The first guide aperture 174 may receive the second end 134 of the guide member 108. The second end 134 may include a smooth, cylindrical outer surface that rotates freely within the second guide aperture 198. The second end 134 may couple with the end coupler 128.

Figure 16:
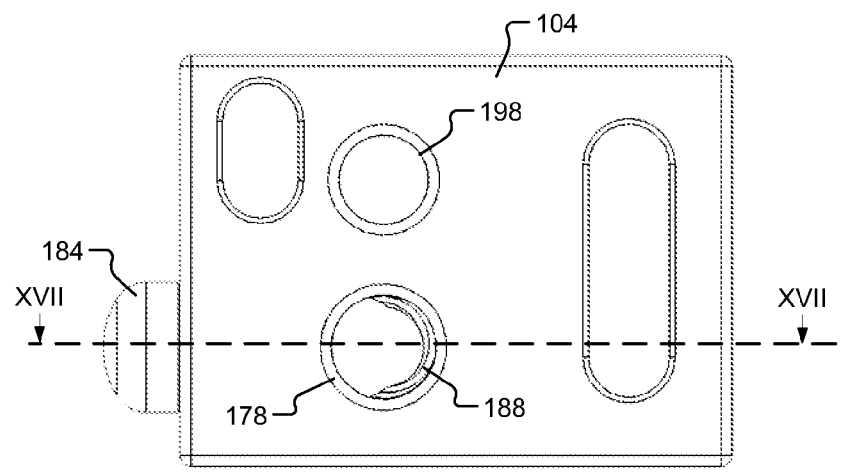
FIG. 16 is a side view of a portion of the instrument according to the principles of the present disclosure.
Figure 17:
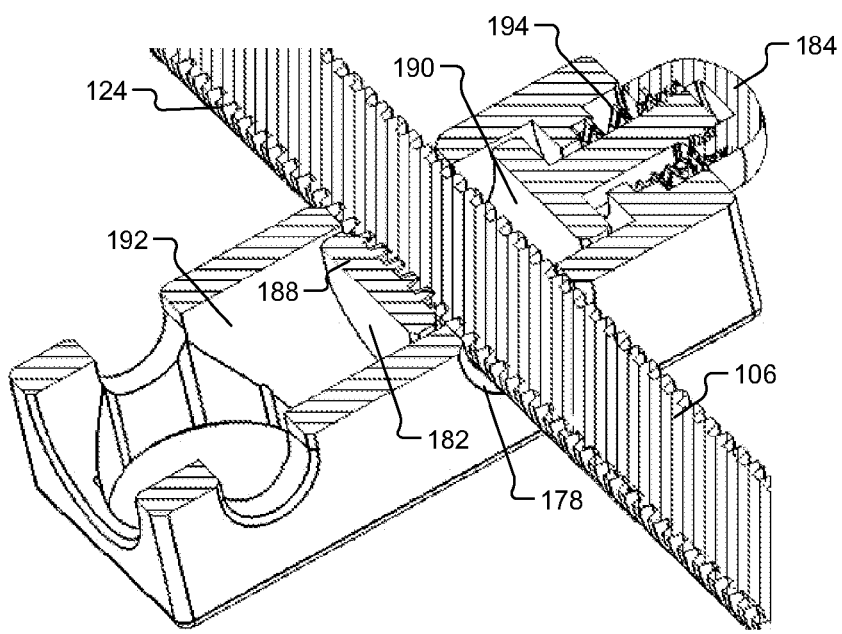
FIG. 17 is a partial cross-sectional view of the portion of the instrument of FIG. 16 engaging another portion of the instrument, looking into a plane XVII according to the principles of the present disclosure.

FIGS. 16-19 illustrate actuation of the release member 180 between an engaged configuration and a released configuration. In FIGS. 16 and 17, the release actuator 184 may position the sleeve 182 to engage the threaded portion 188 with the threaded portion 124 of the positioner member 106 in the engaged configuration. The release spring 194 may bias the sleeve 182 into engagement. With the threaded portions 124 and 188 engaged, rotating the positioner member 106 translates the second receiver 104 along the length of the threaded portion 124. The surgeon may also apply compression and distraction forces on attached screw extenders 20 and 30 as described in FIGS. 1 and 2 by rotating the positioner member 106. The threaded engagement maintains the position of the second receiver 104 as the surgeon performs incremental adjustments.

Figure 18:
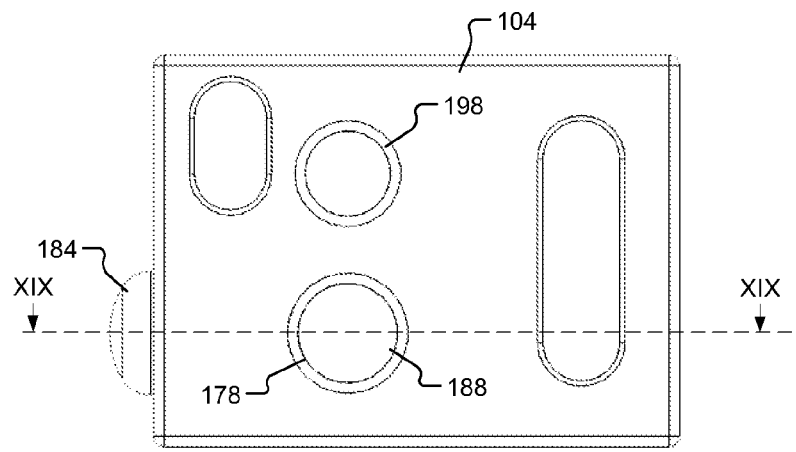
FIG. 18 is a side view of a portion of the instrument according to the principles of the present disclosure.
Figure 19:
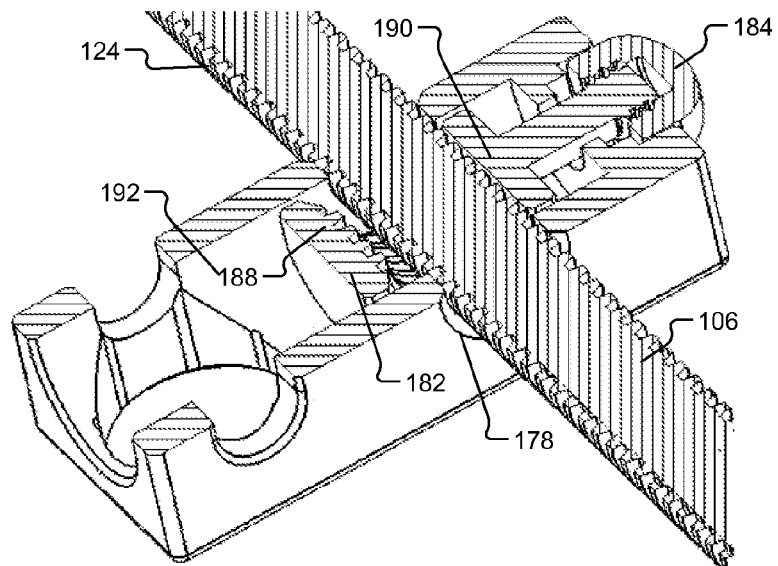
FIG. 19 is a partial cross-sectional view of the portion of the instrument of FIG. 18 engaging another portion of the instrument, looking into a plane XIX according to the principles of the present disclosure.
Figure 20:
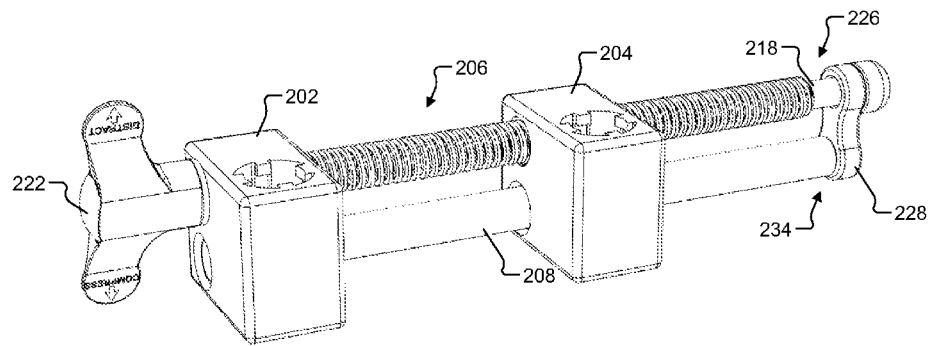
FIG. 20 is a perspective view of another exemplary instrument according to the principles of the present disclosure.
Figure 21:
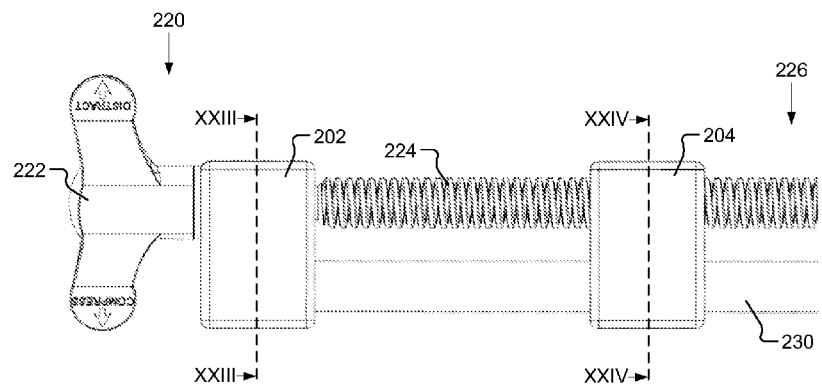
FIG. 21 is a front view of the instrument of FIG. 20 according to the principles of the present disclosure.

In some situations, the surgeon may prefer to position the second receiver 104 more quickly than by rotating the positioner member 106. For example, prior to attaching the instrument 100 to the screw extenders 20 and 30, the second receiver 104 may be too close or too far from the first receiver 102 to attach to the screw extenders 20 and 30. The release member 180 may be positioned into the released configuration to quickly move the second receiver 104 along the length of the threaded portion 124. In FIGS. 18 and 19, the release actuator 184 may be depressed to position the sleeve 182 to disengage the threaded portion 188 from the threaded portion 124 of the positioner member 106 in the released configuration. The non-threaded portion 190 may engage the threaded portion 124 of the positioner member 106 as well. The release spring 194 may compress as the sleeve 182 advances into the release aperture 192. With the threaded portions 124 and 188 disengaged, rotating the positioner member 106 no longer translates the second receiver 104 along the length of the threaded portion 124. The surgeon may freely translate the second receiver 104 to quickly position the instrument 100 for attachment to the screw extenders 20 and 30.

FIGS. 20-25 illustrate another exemplary instrument 200 for compression and distraction of the vertebrae V1 and V2 of the spinal column 10 according to the principles of the present disclosure. The instrument 200 shares some similar features as the instrument 100 of FIGS. 1-19 which are denoted with similar numerals throughout. For example, the instrument 200 includes a first receiver 202 and a second receiver 204 for attachment of the extenders 20 and 30 as well as positioning to provide appropriate compression and distraction forces on the vertebrae V1 and V2. The instrument 200 may translate the second receiver 204 relative to the first receiver 202. For example, the instrument 200 may include a positioner member 206 and a guide member 208. The first receiver 202 may include a first extension member aperture 214 for receiving the first extender 20. The second receiver 204 may include a second extension member aperture 216 for receiving the second extender 30. The positioner member 206 positions the second receiver 204 relative to the first receiver 202 in a first direction along a longitudinal axis of the positioner member 206. The guide member 208 guides the second receiver 204 and prevents rotation about the positioner member 206 as it rotates to position the second receiver 204.

The positioner member 206 may include a first shaft 218 with a first end 220 that extends through the first receiver 202 and terminates in an adjuster 222 or knob. The first end 220 may rotate freely within the first receiver 202. The adjuster 222 may be used to rotate the positioner member 206. The adjuster 222 may be secured to the first end 220 with a lock pin. The shaft 218 may include a threaded portion 224 that engages with features within the second receiver 204. The threaded portion 224 may rotate in a first direction to position the second receiver 204 away from the first receiver 202 and a second opposite direction to position the second receiver 204 towards the first receiver 202. A second end 226 of the positioner member 206 may couple with an end coupler 228. The second end 226 may rotate freely within the end coupler 228.

The guide member 208 extends through the first and second receivers 202 and 204 and guides the movement of the second receiver 104. The guide member 208 may include a second shaft 130 with a first end 132 received by the first receiver 102. The second shaft 230 may include a substantially smooth, cylindrical surface. The first end 232 may be secured within the first receiver 202 with a lock pin. The guide member 208 extends away from the first receiver 202 and through the second receiver 204 substantially parallel to the positioner member 206. A second end 234 of the second shaft 230 may couple with the end coupler 228. The second end 234 may be secured by the end coupler 228. The shaft 230 may include markings indicating distances between the first and second receivers 202 and 204.

Figure 22:
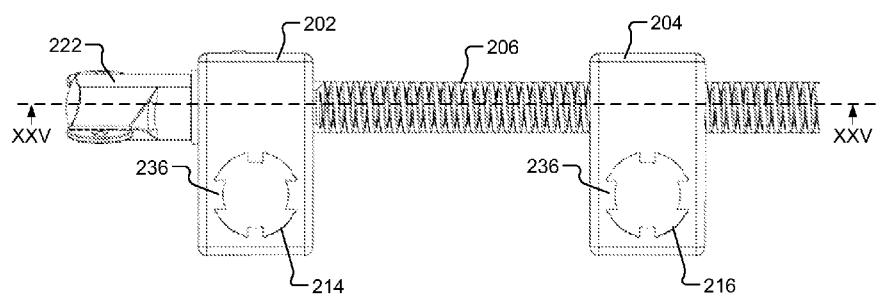
FIG. 22 is a top view of the instrument of FIG. 20 according to the principles of the present disclosure.

The instrument 200 may include attachment features for quick attachment to and removal from the extenders 20 and 30. For example, as illustrated in FIG. 22, radial tabs 236 may extend radially inward from sidewalls of the apertures 214 and 216. The radial tabs 236 may be configured to engage the proximally extending tabs 24 and 34 on the proximal ends of the first and second extenders 20 and 30. Each aperture may include a plurality of radial tabs 236. For example, the radial tabs 236 may be aligned at approximately 90 degree intervals around the apertures 214 and 216. The tabs 236 may restrict rotation of the extenders 20 and 30 within the apertures 214 and 216.

Figure 23:
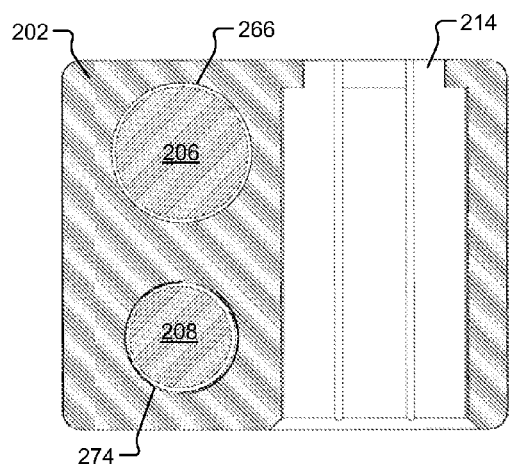
FIG. 23 is a cross-sectional view of the instrument of FIG. 21 looking into a plane XXIII according to the principles of the present disclosure.
Figure 24:
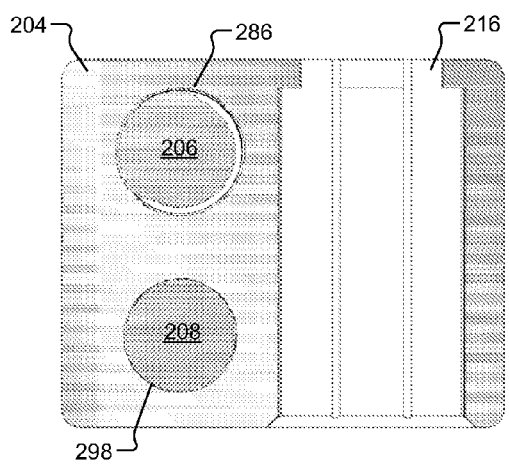
FIG. 24 is a cross-sectional view of the instrument of FIG. 21 looking into a plane XXIV according to the principles of the present disclosure.
Figure 25:
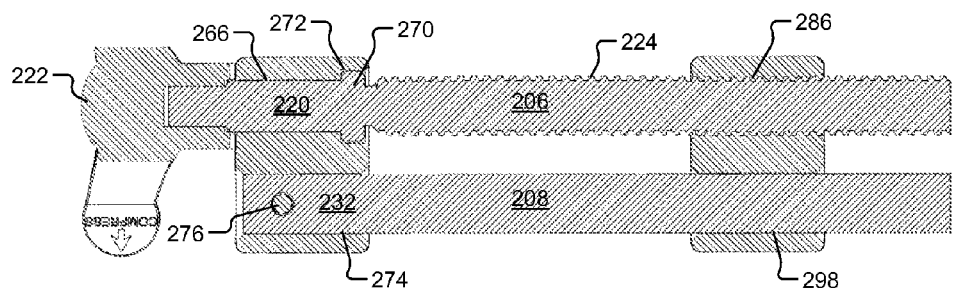
FIG. 25 is a cross-sectional view of the instrument of FIG. 22 looking into a plane XXV according to the principles of the present disclosure.
Figure 26:
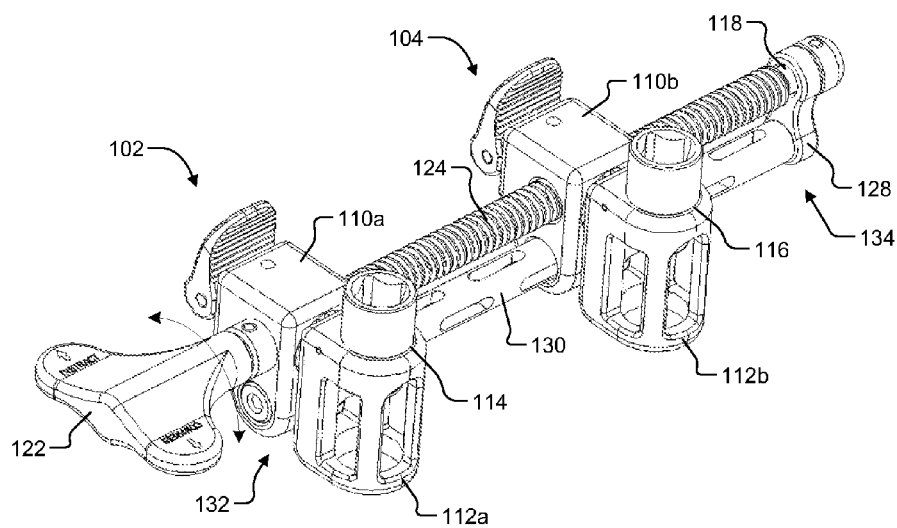
FIGS. 26-29 illustrate the instrument including a non-translatable receiver with a first rotatable portion and a translatable receiver with a second rotatable portion according to the principles of the present disclosure.
Figure 27:
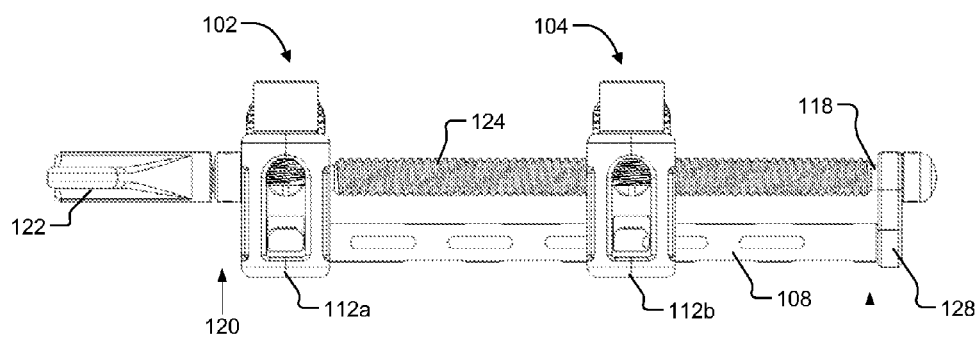
Figure 28:
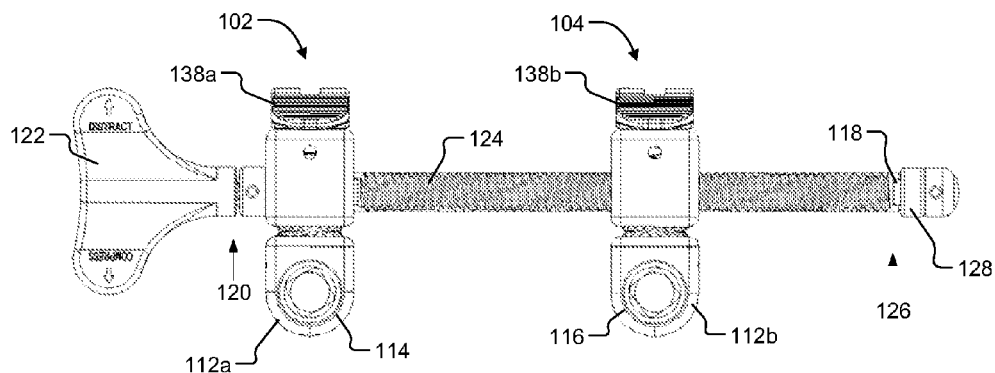

Referring now to FIGS. 23-25, cross-sectional views of the instrument 200 illustrate features for receiving the positioner member 206 and guide member 208. The first receiver 202 includes a first positioner aperture 266 and first guide aperture 274. The second receiver 204 includes a second positioner aperture 286 and a second guide aperture 298. The second positioner aperture 286 may be threaded to engage with a threaded portion 224 of the positioner member 206.

Referring now to FIGS. 26-29, the instrument 100 includes the first receiver 102, the second receiver 104, and the positioner member 106 as described with reference to FIGS. 2-5. The first receiver 102 may attach to the first extender 20 and the second receiver 104 may attach to the second extender 30 of FIG. 1. The extenders 20, 30 may include various features that limit rotational or translational movement when attached to the instrument 100. For example, the extenders 20, 30 may include threading that engages coupling screws 220, 230. The positioner member 106 may position at least one of the first and second receivers 102 and 104. For example, the positioner member 106 may translate the second receiver 104 relative to the first receiver 102. The guide member 108 may guide the movement of at least one of the first and second receivers 102 and 104. For example, the guide member 108 may extend parallel to the positioner member 106 and through the second receiver 104 to guide its movement relative to the first receiver 102. Like numbers are used throughout FIGS. 26-29 to reference the same or similar elements as FIGS. 1-7.

In the present example of the instrument 100, both the first receiver 102 and the second receiver 104 may include rotatable portions 112a and 112b (collectively rotatable portions 112). The rotatable portions 112 may rotate or pivot to various angles relative to the fixed (translatable) portion 110b of the second receiver 104 and the fixed (non-translatable) portion 110a of the first receiver 102 respectively. That is, both the first and second receivers 102 and 104 may include fixed portions 110a and 110b (collectively fixed portions 110) that are rotatably fixed relative to the guide member 108. The rotatable portions 112 may include the first extension member aperture 114 for receiving the first extender 20 and the second extension member aperture 116 for receiving the second extender 30. The fixed (translatable) portion 110b and the fixed (non-translatable) portion 110a may receive the positioner member 106 and the guide member 108. The positioner member 106 positions the second receiver 104 relative to the first receiver 102 in a first direction along a longitudinal axis of the positioner member 106. The guide member 108 guides the second receiver 104 and prevents rotation about the positioner member 106 as it rotates to position the second receiver 104.

The positioner member 106 may include the first shaft 118 with the first end 120 that extends through the first receiver 102 and terminates in the adjuster 122 or knob. The first end 120 may rotate freely within the first receiver 102. The adjuster 122 may be used to rotate the positioner member 106. The adjuster 122 may be secured to the first end 120 with a lock pin. The shaft 118 may include a threaded portion 124 that engages with features within the second receiver 104. The threaded portion 124 may rotate in a first direction to position the second receiver 104 away from the first receiver 102 and a second opposite direction to position the second receiver 104 towards the first receiver 102. The second end 126 of the positioner member 106 may couple with the end coupler 128. The second end 126 may rotate freely within the end coupler 128.

The guide member 108 extends through the first and second receivers 102 and 104 and guides the movement of the second receiver 104. The guide member 108 may include the second shaft 130 with the first end 132 received by the first receiver 102. The second shaft 130 may include a substantially smooth, cylindrical surface. The first end 132 may be secured within the first receiver 102 with a lock pin. The guide member 108 extends away from the first receiver 102 and through the second receiver 104 substantially parallel to the positioner member 106. The second end 134 of the second shaft 130 may couple with the end coupler 128. The second end 134 may be secured by the end coupler 128. The shaft 130 may include markings indicating distances between the first and second receivers 102 and 104. The instrument 100 may couple with the screw extenders 20 and 30 using coupling screws 220, 230.

Figure 29:
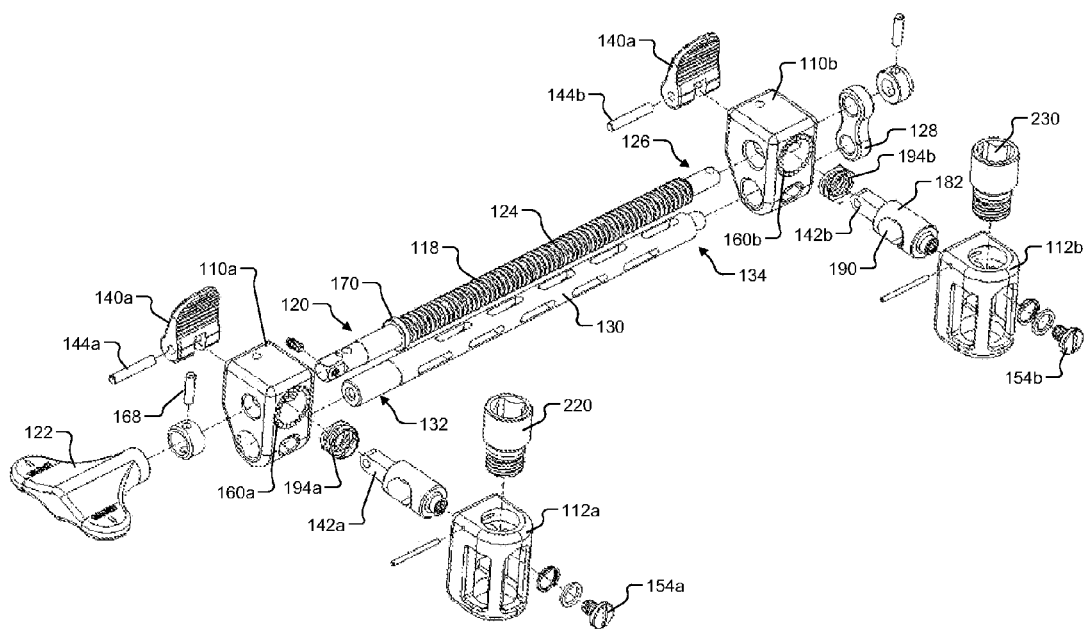

FIG. 29 is an exploded view of the instrument 100 illustrating various examples of features that permit the rotational positioning of the first receiver 102 and the second receiver 104. For example, the first receiver 102 includes the first rotatable portion 112a and the fixed (non-translatable) portion 110a. Each receiver may include a lock member similar to lock member 138. For example, a first lock member 138a may couple the fixed portion 110a and the rotatable portion 112a. The lock member 138a may include a lock arm 140a and a lock shaft 142a. The lock shaft 142a may extend through the fixed portion 110a and the rotatable portion 112a of the first receiver 102. A lock pin 144a may pivotally couple the lock arm 140a with the lock shaft 142a. The lock arm 140a may engage the fixed portion 110a as it pivots about the lock pin 144a. The lock pin 144a may be located off-center at a base portion of the lock arm 140a. For example, as the lock arm 140a rotates, the lock pin 144a may translate towards or away from the fixed portion 110a, thus moving the attached lock shaft 142a within the fixed portion 110a. Similarly, the second receiver 104 may include the second rotatable portion 112b and the fixed (translatable) portion 110b. A second lock member 138b includes the same or similar features of the first lock member 138a.

Similar to the instrument 100 as shown in FIGS. 6 and 7, the exploded view of the instrument 100 in FIG. 29 illustrates various examples of features that facilitate the translational positioning of the second receiver 104 relative to the first receiver 102. For example, the first receiver 102 and second receiver 104 include various apertures and/or bores to receive the positioner member 106 and guide member 108 similar to the instrument 100 as shown in FIGS. 1-7.

The second receiver 104 further includes a release member for releasably engaging the positioner member 106. The release member may be integral with the lock shaft 142b. The release member may include the sleeve 182 and the release actuator 184. The sleeve 182 may include the thru-hole 186 that receives the threaded portion 124 of the positioner member 106. The thru-hole 186 may be formed from two separate, intersecting bores. The first bore may be tapped and the second bore may be smooth. For example, the thru-hole 186 may include the threaded portion (not shown) and the non-threaded portion 190. The threaded portion and the non-threaded portion 190 may be disposed on opposite sides of the thru-hole 186. The release member 180 may slide within the release aperture 192 inside the second receiver 104. The release aperture 192 may communicate with the second positioner aperture 178. The release aperture 192 may extend transverse to the second positioner aperture. A release spring 194b within the release aperture 192 may bias the release member 180. The release spring 194 may engage the release actuator 184 and a narrowed portion 196 or internal ridge of the release aperture 192. The thru-hole 186 may align with the second positioner aperture 178 to permit passage of the positioner member 106 there through.

A second guide aperture 198 through the second receiver 104. The second guide aperture 198 may extend transverse to the release aperture 192 and parallel to the second positioner aperture 178. The second guide aperture 198 may be disposed proximal to the release aperture 192. The first guide aperture 174 may receive the second end 134 of the guide member 108. The second end 134 may include a smooth, cylindrical outer surface that rotates freely within the second guide aperture 198. The second end 134 may couple with the end coupler 128.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. An instrument for compression and distraction of vertebrae using screw extenders, comprising:
   a first receiver including
      a fixed portion with a first positioner aperture and a first guide aperture; and
      a rotatable portion with a first receiver aperture for attachment to a first screw extender;
   a second receiver including a second positioner aperture, a second guide aperture, and a second receiver aperture for attachment to a second extender;
   a positioner member that translates one of the first and second receivers relative to the other of the first and second receivers;

a guide member that guides the translation of the one of the first and second receivers relative to the other of the first and second receivers; and a lock member that disengages the rotatable portion from the fixed portion in the rotatable configuration and engages the rotatable portion with the fixed portion in the fixed configuration, wherein the lock member includes a lock shaft extending through a first lock aperture of the fixed portion and pivotally couples with a lever arm at a first end and a lock cap at a second end within a second lock aperture of the rotatable portion.

2. The instrument of claim 1, wherein the positioner member includes a shaft with a threaded portion and the guide member is substantially parallel to the positioner member.

3. The instrument of claim 1, wherein the rotatable portion is rotatable relative to the fixed portion in a rotatable configuration and is rotatably fixed relative to the fixed portion in a fixed configuration.

4. The instrument of claim 1, wherein the fixed portion includes a first surface with a first plurality of projections that mates with a second plurality of projections on a second surface of the rotatable portion.

5. The instrument of claim 1, further comprising a release member that disengages the second receiver from the positioner member in a released configuration and engages the second receiver with the positioner member in an engaged configuration.

6. The instrument of claim 5, wherein the second receiver freely slides along the positioner member and guide member when the release member is in the released configuration and threadably moves along the positioner member in the engaged configuration.

7. The instrument of claim 5, wherein the release member includes a partially threaded sleeve slidably extending through a release aperture of the second receiver and coupled with a release button and bias spring that biases the release member into the engaged configuration.

8. An instrument for compression and distraction of vertebrae using screw extenders, comprising:
   a translatable receiver including a translatable portion and a first rotatable portion with a first extender aperture configured to receive a first screw extender;
   a non-translatable receiver including non-translatable portion and a second rotatable portion with a second extender aperture configured to receive a second screw extender;
   a guide member including a first end coupled with the non-translatable portion and a second end slidably coupled with the translatable portion;
   a positioner member including a first end rotatably coupled with the non-translatable portion and a second end threaddedly coupled with the translatable portion;
   first and second lock members that lock the first and second rotatable portions at first and second predetermined angles relative to the guide member in an locked configuration and permit rotation of the first and second rotatable portions relative to the guide member in an unlocked configuration; and
   a release member coupling the translatable receiver with the positioner member including:
      a sleeve having a threaded portion and a non-threaded portion that slides within the translatable portion; and
      a bias member that biases the threaded portion of the sleeve into threaded engagement with the positioner member in an engaged configuration and disengages the threaded portion from the positioner member when moved to a slidable configuration.

\* \* \* \* \*